United States Patent
Lin et al.

(10) Patent No.: US 11,066,637 B1
(45) Date of Patent: Jul. 20, 2021

(54) PARTICULATE STRUCTURE WITH A HIGH CONCENTRATION OF LIVE BACTERIA AND METHOD OF PREPARING THE SAME

(71) Applicant: TCI Co., Ltd., Taipei (TW)

(72) Inventors: Yung-Hsiang Lin, Taipei (TW); Cheng-Yu Ho, Taipei (TW); Jin-Jia Wang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 16/826,892

(22) Filed: Mar. 23, 2020

(30) Foreign Application Priority Data

Dec. 25, 2019 (TW) .................................. 108147675

(51) Int. Cl.
| | | |
|---|---|---|
| *C12N 1/00* | (2006.01) | |
| *C12N 1/04* | (2006.01) | |
| *C12N 1/20* | (2006.01) | |
| *A61K 35/741* | (2015.01) | |

(52) U.S. Cl.
CPC .................. *C12N 1/04* (2013.01); *C12N 1/20* (2013.01); *A61K 35/741* (2013.01)

(58) Field of Classification Search
CPC ....................................................... C12N 1/04
See application file for complete search history.

(56) References Cited

U.S. PATENT DOCUMENTS 5,939,295 A * 8/1999 Dunkak ......... C12Y 401/01048
435/108

FOREIGN PATENT DOCUMENTS

| CN | 102220272 A | 10/2011 |
|---|---|---|
| CN | 102978143 B | 4/2014 |
| WO | WO 2010/054439 A1 | 5/2010 |

OTHER PUBLICATIONS

Hubálek, Zdenek, "Protectants used in the cryopreservation of microorganisms," *Cryobiology*, vol. 46, pp. 205-229 (2003).

* cited by examiner

*Primary Examiner* — Albert M Navarro
*Assistant Examiner* — Mark Navarro
(74) *Attorney, Agent, or Firm* — Christensen, Fonder, Dardi & Herbert PLLC

(57) ABSTRACT

A live bacteria-containing particulate is provided, wherein the particulate comprises a bacterial strain, a first covering layer, and a second covering layer, and wherein the first covering layer is in-between the cell membrane and cell wall of the bacterial strain and the bacterial strain is dispersed in the second covering layer. A method of preparing a live bacteria-containing particulates is also provided, wherein the method comprises the following steps: (a) subjecting a bacterial strain to a three-stage fermentation to obtain a fermentation broth; (b) concentrating the fermentation broth to provide a concentrated bacterial solution; (c) mixing the concentrated bacterial solution with a protective agent; and (d) drying the mixture to provide live bacteria-containing particulates.

8 Claims, 5 Drawing Sheets

PARTICULATE STRUCTURE WITH A HIGH CONCENTRATION OF LIVE BACTERIA AND METHOD OF PREPARING THE SAME

CROSS REFERENCE TO RELATED APPLICATIONS

This application claims priority to Taiwan Patent Application No. 108147675 filed on Dec. 25, 2019, in the Taiwan Intellectual Property Office, the disclosures of which are incorporated herein in their entirety by reference.

FIELD OF THE INVENTION

The present invention relates to a live bacteria-containing particulate, comprising a bacterial strain, a first covering layer, and a second covering layer, wherein the first covering layer is in-between the cell membrane and cell wall of the bacterial strain and the bacterial strain is dispersed in the second covering layer. The present invention also relates to a method of preparing a live bacteria-containing particulates, comprising the following steps: (a) subjecting a bacterial strain to a three-stage fermentation to obtain a fermentation broth; (b) concentrating the fermentation broth to provide a concentrated bacterial solution; (c) mixing the concentrated bacterial solution with a protective agent; and (d) drying the mixture to provide live bacteria-containing particulates.

BACKGROUND OF THE INVENTION

Alongside people's understanding of probiotics and their effect(s) on human health, the use of probiotic products is increasing daily. Due to specific needs of maintaining probiotic activity, there are many limitations for storing the live bacteria-containing probiotic products, for example, storing at a refrigerating temperature, a freezing temperature or packaged in a modified atmosphere. Furthermore, due to specific needs related to the convenience of transport and storage, the probiotic products are usually provided in a form of bacteria powder (e.g., live bacteria-containing particulates).

Spray-drying and freeze-drying are common drying methods for preparing bacteria powder. However, the spray-drying should be conducted at a high temperature, and thus may kill live bacteria in the bacteria powder; and the ice crystals that formed during the freezing process of freeze-drying may also damage bacteria, thereby the viable bacterial count (VBC) in the bacteria powder decreases. Therefore, the industry currently focuses on developing a method of preparing a bacteria powder with a high viable bacterial count.

Regarding the above technical problems, inventors of the present invention found a method of providing a bacterial solution with a high concentration of live bacteria, a method of preparing live bacteria-containing particulates, and a live bacteria-containing particulate with a high viable bacterial count and low residual moisture.

SUMMARY OF THE INVENTION

An objective of the present invention is to provide a method of providing a bacterial solution with a high concentration of live bacteria, comprising
(a) subjecting a bacterial strain to a three-stage fermentation to obtain a fermentation broth, wherein the three-stage fermentation comprises:
subjecting a broth of the bacterial strain with a volume of V1 to a first fermentation stage for t1 hour to provide a first-stage fermentation broth, $T_1-2 \leq t1 \leq T_1+2$, and t1 is no less than 0.5,
diluting and subjecting the first-stage fermentation broth to a second fermentation stage for t2 hour to provide a second-stage fermentation broth, wherein the first-stage fermentation broth is diluted to a volume of V2, $V2/V1=10\sim35$, $T_1-2 \leq t2 \leq T_1+2$, and t2 is no less than 0.5, and
diluting and subjecting the second-stage fermentation broth to a third fermentation stage for t3 hour to provide a third-stage fermentation broth, wherein the second-stage fermentation broth is diluted to a volume of V3, $V3/V2=10\sim35$, $T_2-2 \leq t3 \leq T_2+2$, and t3 is no less than 0.5,
and wherein,
$T_1$ is an initial time point of growth logarithmic phase of the strain, and
$T_2$ is an initial time point of growth stationary phase of the strain; and
(b) concentrating the third-stage fermentation broth to provide a concentrated bacterial solution.

Another objective of the present invention is to provide a method of preparing live bacteria-containing particulates, comprising
(a) subjecting a bacterial strain to a three-stage fermentation to obtain a fermentation broth, wherein the three-stage fermentation comprises:
subjecting a broth of the bacterial strain with a volume of V1 to a first fermentation stage for t1 hour to provide a first-stage fermentation broth, $T_1-2 \leq t1 \leq T_1+2$, and t1 is no less than 0.5,
diluting and subjecting the first-stage fermentation broth to a second fermentation stage for t2 hour to provide a second-stage fermentation broth, wherein the first-stage fermentation broth is diluted to a volume of V2, $V2/V1=10\sim35$, $T_1-2 \leq t2 \leq T_1+2$, and t2 is no less than 0.5, and
diluting and subjecting the second-stage fermentation broth to a third fermentation stage for t3 hour to provide a third-stage fermentation broth, wherein the second-stage fermentation broth is diluted to a volume of V3, $V3/V2=10\sim35$, $T_2-2 \leq t3 \leq T_2+2$, and t3 is no less than 0.5,
and wherein,
$T_1$ is an initial time point of growth logarithmic phase of the strain, and
$T_2$ is an initial time point of growth stationary phase of the strain,
(b) concentrating the third-stage fermentation broth to provide a concentrated bacterial solution;
(c) mixing the concentrated bacterial solution with a protective agent to provide a mixture; and
(d) drying the mixture to obtain live bacteria-containing particulates.

Preferably, in the above methods of providing a bacterial solution with a high concentration of live bacteria and preparing live bacteria-containing particulates, $T_1-1 \leq t1 \leq T_1+1$, $T_1-1 \leq t2 \leq T_1+1$ and $T_2-2 \leq t3 \leq T_2$.

Still another objective of the present invention is to provide a live bacteria-containing particulate, which is provided by the methods described above.

Yet another objective of the present invention is to provide a live bacteria-containing particulate, comprising a bacterial strain, a first covering layer, and a second covering layer, wherein the first covering layer is in-between the cell membrane and cell wall of the bacterial strain and the bacterial strain is dispersed in the second covering layer. Preferably, the particulate further comprises a third covering layer, and the third covering layer is outside the second covering layer.

In the live bacteria-containing particulate provided in accordance with the present invention, the first covering layer comprises at least one of isomalto-oligosaccharide (IMO), lactose, trehalose, galactose, fructose, glucose, maltose, sucrose, fructooligosaccharide (FOS), rhamnose and raffinose; the second covering layer comprises at least one of maltodextrin, skim milk powder, inulin and starch; and the third covering layer comprises at least one of maltodextrin, arabic gum, chocolate and skim milk powder.

The detailed technology and preferred embodiments implemented for the present invention are described in the following paragraphs accompanying the appended drawings for persons skilled in the art to well appreciate the features of the claimed invention.

DESCRIPTION OF THE PREFERRED EMBODIMENT

Figure 1:
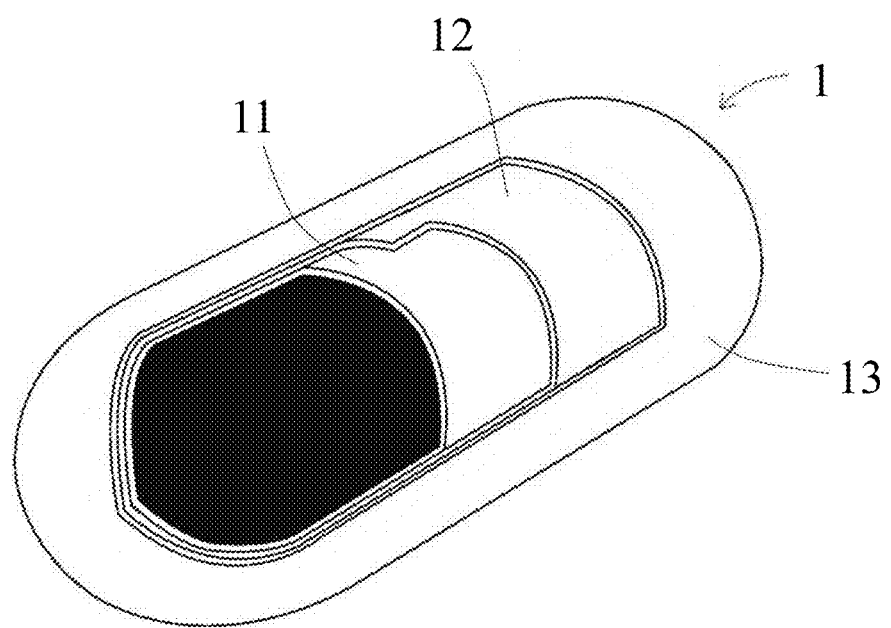
FIG. 1 shows the relative position of the first covering layer and the cell membrane and cell wall of the bacterial strain in the live bacteria-containing particulate of the present invention.

The following paragraphs will describe some of the embodiments of the present invention in detail. However, without departing from the spirit of the present invention, the present invention may be embodied in various embodiments and should not be limited to the embodiments described in the specification.

Unless otherwise indicated herein, the expression "a," "an," "the," or the like recited in the specification of the present invention (especially in the claims) are intended to include both the singular and plural forms; the term "oligosaccharide" recited herein refers to a glycan possessing 2 to 10 monosaccharide units; the term "polysaccharide" recited herein refers to a glycan possessing more than 10 monosaccharide units; the term "low residual moisture" recited herein refers to that based on the total weight of live bacteria-containing particulates, the residual moisture is less than 10 wt %.

The numerical ranges (e.g., 5 to 100) recited in this specification should be construed as including all the rational numbers in the ranges as well as the ranges consisting of any rational numbers in the ranges. Therefore, the numerical ranges recited in this specification should include all the possible combinations of numerical values between the lowest value and the highest value listed therein. In addition, the word "about" present before the values as used herein substantially represents that the values can be increased or decreased by a normal and reasonable amount determined by what a person having ordinary skill in the art would consider acceptable. For example, the word "about" present before the values as used herein substantially represents values within ±10% of the stated value and more preferably within ±5%.

The terms such as "first covering layer", "second covering layer" and "third covering layer" recited herein are only to distinguish different covering layers, but not to limit the covering layers.

Depending on the growth rate of bacteria, the bacterial growth cycle can be divided into lag phase, logarithmic phase, stationary phase and decline/death phase. Inventors of the present invention discovered that the time cost for the scale-up fermentation could be effectively reduced by controlling the bacterial growth cycle during the bacterial fermentation, thereby a bacterial solution with a high concentration of live bacteria could be provided in a short time period. Inventors of the present invention also discovered that mixing the bacterial solution with a high concentration of live bacteria, provided in accordance with the present invention, with a protective agent and further drying the mixture can provide a live bacteria-containing particulate with a high viable bacterial count and a low residual moisture. Therefore, the present invention relates to a live bacteria-containing particulate and a method of preparing the same. The present invention includes a method of providing a bacterial solution with a high concentration of live bacteria, a method of preparing live bacteria-containing particulates, and a live bacteria-containing particulate.

The term "growth logarithmic phase" recited herein refers to a period in the bacterial growth cycle during which the bacterial count dramatically increases; the term "growth stationary phase" recited herein refers to a period in the bacterial growth cycle during which the bacterial count maintains a constant value. In the present invention, an initial time point of growth logarithmic phase (hereinafter referred to as "$T_1$") and an initial time point of growth stationary phase (hereinafter referred to as "$T_2$") are determined based on the bacterial growth curve, wherein, $T_1$ refers to a time point whose tangent line slope is equal to or more than three times of that at an hour ago, and $T_2$ refers to a time point whose tangent line slope is 0 (zero).

1. METHOD OF PROVIDING A BACTERIAL SOLUTION WITH A HIGH CONCENTRATION OF LIVE BACTERIA

The present invention relates to a method of providing a bacterial solution with a high concentration of live bacteria, comprising
(a) subjecting a bacterial strain to a three-stage fermentation to obtain a fermentation broth, wherein the three-stage fermentation comprises:
  subjecting a broth of the bacterial strain with a volume of V1 to a first fermentation stage for t1 hour to provide a first-stage fermentation broth, $T_1-2 \leq t1 \leq T_1+2$, and t1 is no less than 0.5,
  diluting and subjecting the first-stage fermentation broth to a second fermentation stage for t2 hour to provide a second-stage fermentation broth, wherein the first-stage fermentation broth is diluted to a volume of V2, V2/V1=10~35, $T_1-2 \leq t2 \leq T_1+2$, and t2 is no less than 0.5, and
  diluting and subjecting the second-stage fermentation broth to a third fermentation stage for t3 hour to provide a third-stage fermentation broth, wherein the second-stage fermentation broth is diluted to a volume of V3, V3/V2=10~35, $T_2-2 \leq t3 \leq T_2+2$, and t3 is no less than 0.5, and wherein, $T_1$ is an initial time point of growth logarithmic phase of the strain, and $T_2$ is an initial time point of growth stationary phase of the strain; and (b) concentrating the third-stage fermentation broth to provide a concentrated bacterial solution.

The method in accordance with the present invention described above can be used for any suitable bacterial strain, and particularly probiotics. Examples of the bacterial strain include, but are not limited to, *Streptococcus thermophiles*, *Bifidobacterium longum*, *Lactobacillus plantarum*, *Bacillus coagulans*, *Lactobacillus casei*, *Lactobacillus helveticus*, *Lactobacillus gasseri*, *Bifidobacterium lactis*, *Lactobacillus johnsonii*, *Pediococcus acidilactici*, *Lactobacillus fermentum*, *Lactobacillus rhamnosus*, *Saccharomyces cerevisiae*, *Lactobacillus paracasei*, *Leuconostoc mesenteroides*, *Lactobacillus salivarius*, *Lactobacillus delbrueckii* and *Lactobacillus brevis*. In an embodiment of the present invention, a bacterial solution with a high concentration of *Lactobacillus plantarum* was provided by the method described above.

In step (a), t1 is ranging from two hours before to two hours after the initial time point of growth logarithmic phase (i.e., $T_1-2 \leq t1 \leq T_1+2$); t2 is also ranging from two hours before to two hours after the initial time point of growth logarithmic phase (i.e., $T_1-2 \leq t2 \leq T_1+2$); t3 is ranging from two hours before to two hours after the initial time point of growth stationary phase (i.e., $T_2-2 \leq t3 \leq T_2+2$); and t1, t2 and t3 all are no less than 0.5. Preferably, t1 is ranging from one hour before to one hour after the initial time point of growth logarithmic phase (i.e., $T_1-1 \leq t1 \leq T_1+1$); t2 is ranging from one hour before to one hour after the initial time point of growth logarithmic phase (i.e., $T_1-1 \leq t2 \leq T_1+1$); t3 is ranging from two hours before the initial time point of growth stationary phase to the initial time point (i.e., $T_2-2 \leq t3 \leq T_2$); and t1, t2 and t3 all are no less than 0.5. In an embodiment of the present invention, a bacterial solution with a high concentration of live *Lactobacillus plantarum* was prepared by the method as described above, wherein the $T_1$ was 2 and $T_2$ was 8 (based on the tangent line slope as shown on the growth curve of *Lactobacillus plantarum*), and thus, $0.5 \leq t1 \leq 4$, $0.5 \leq t2 \leq 4$, and $6 \leq t3 \leq 10$. Preferably, in the method of providing a bacterial solution with a high concentration of live *Lactobacillus plantarum* in accordance with the present invention, the first fermentation stage was conducted for 2 to 3 hours (i.e., t1 is 2 to 3) the second fermentation stage was conducted for 2 to 4 hours (i.e., t2 is 2 to 4), and the third fermentation stage was conducted for 6 to 8 hours (i.e., t3 is 6 to 8).

Preferably, in the method of providing a bacterial solution with a high concentration of live bacteria in accordance with the present invention, the volume of second-stage fermentation broth (V2) is 10 to 25 times of the volume of first-stage fermentation broth (V1) (i.e., V2/V1=10~25), and the volume of third-stage fermentation broth (V3) is 10 to 30 times of the volume of second-stage fermentation broth (i.e., V3/V2=10~30).

In step (a), depending on the type of bacterial strain, the culture temperature and fermentation medium can be adjusted. For example, *Streptococcus thermophiles*, *Bacillus coagulans*, *Lactobacillus delbrueckii* can be cultured at a temperature of 42° C.±5; *Saccharomyces cerevisiae* and *Leuconostoc mesenteroides* can be cultured at a temperature of 30° C.±5; *Streptococcus thermophiles*, *Bifidobacterium longum*, *Lactobacillus plantarum*, *Lactobacillus casei*, *Lactobacillus helveticus*, *Lactobacillus gasseri*, *Bifidobacterium lactis*, *Lactobacillus johnsonii*, *Pediococcus acidilactici*, *Lactobacillus fermentum*, *Lactobacillus rhamnosus*, *Lactobacillus paracasei*, *Lactobacillus salivarius* and *Lactobacillus brevis* can be cultured at a temperature of 37° C.±5. As for the fermentation medium, for example, the fermentation medium suitable for *Lactobacillus plantarum* can be provided by using pure water as a base of the medium by evenly mixing each liter of pure water with 20 to 40 g of yeast extract, 10 to 30 g of yeast peptone, 1 to 3 g of dipotassium phosphate, 0.5 to 1.5 g of magnesium sulfate, 0.5 to 1.5 g of polysorbate 80, 10 to 30 g of glucose and 10 to 30 g of 10N sodium hydroxide.

In step (b), the fermentation broth obtained from step (a) can be concentrated by using any suitable centrifugal apparatus without particular limitations, as long as the centrifugal apparatus can effectively reduce the volume of fermentation broth and keep the live bacteria in the bacterial solution. Preferably, the fermentation broth is at least 10× concentrated (i.e., the volume of concentrated bacterial solution is no greater than one-tenth of the volume of fermentation broth). For example, a 500 L fermentation broth is concentrated to be a 30~50 L concentrated bacterial solution.

2. METHOD OF PREPARING LIVE BACTERIA-CONTAINING PARTICULATES

The present invention also relates to a method of preparing live bacteria-containing particulates, which comprises subjecting the concentrated bacterial solution provided by the above method (i.e., "1. Method of providing a bacterial solution with a high concentration of live bacteria") to the following processes:

(c) mixing the concentrated bacterial solution with a protective agent to provide a mixture, and (d) drying the mixture to obtain live bacteria-containing particulates.

The purpose of step (c) is to protect the live bacteria from damage or even death caused by the drying process of step (d) by mixing the concentrated bacterial solution with a protective agent. Thus, any suitable protective agent can be used in step (c) without particular limitations, as long as the protective agent can effectively protect the live bacteria in the concentrated bacterial solution during the drying process. Examples of the suitable protective agent of step (c) include, but is not limited to isomalto-oligosaccharide (IMO), lactose, trehalose, galactose, fructose, glucose, maltose, sucrose, fructooligosaccharide (FOS), rhamnose, raffinose, maltodextrin, skim milk powder, inulin, starch, arabic gum and chocolate.

Preferably, the protective agent used in step (c) comprises at least one oligosaccharide (e.g., isomalto-oligosaccharide (IMO), lactose, trehalose, galactose, fructose, glucose, maltose, sucrose, fructooligosaccharide (FOS), rhamnose and raffinose) and at least one polysaccharide (e.g., maltodextrin, inulin and starch) or protein (e.g., skim milk powder), wherein the oligosaccharide is semi-permeable to bacterial cells (i.e., the oligosaccharide can permeate into a space between the cell wall and cell membrane of bacteria). More preferably, the protective agent used in step (c) further comprises at least one moisture-proof agent (e.g., maltodextrin, arabic gum, chocolate and skim milk powder). For example, the protective agent used in step (c) comprises lactose, inulin and maltodextrin, or comprises lactose, maltodextrin and skim milk powder.

In step (d), any suitable drying method can be used to dry the mixture provided by step (c), such as a spray-drying and freeze-drying, but is not limited thereby. In an embodiment of the present invention, in step (d), the mixture provided by step (c) is dried by using freeze-drying, to provide a live bacteria-containing particulate.

3. LIVE BACTERIA-CONTAINING PARTICULATES

Figure 2:
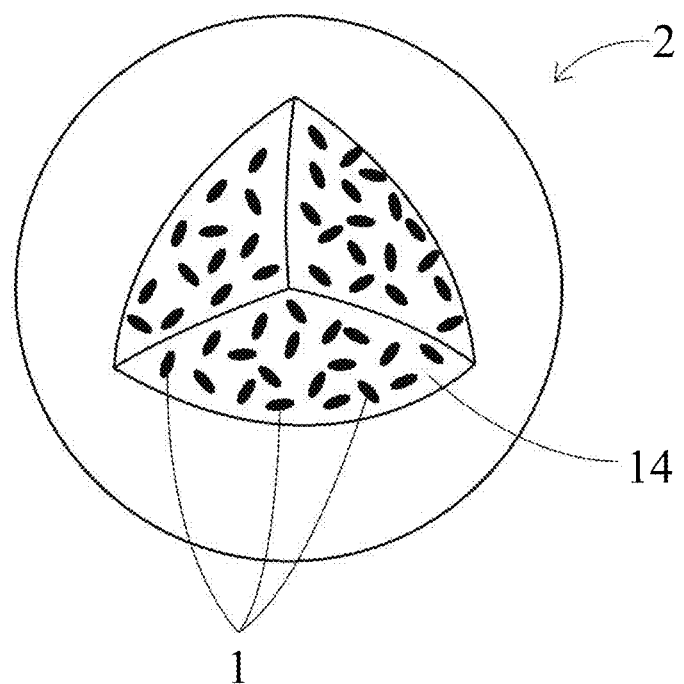
FIG. 2 is an embodiment of the live bacteria-containing particulate of the present invention.
Figure 3:
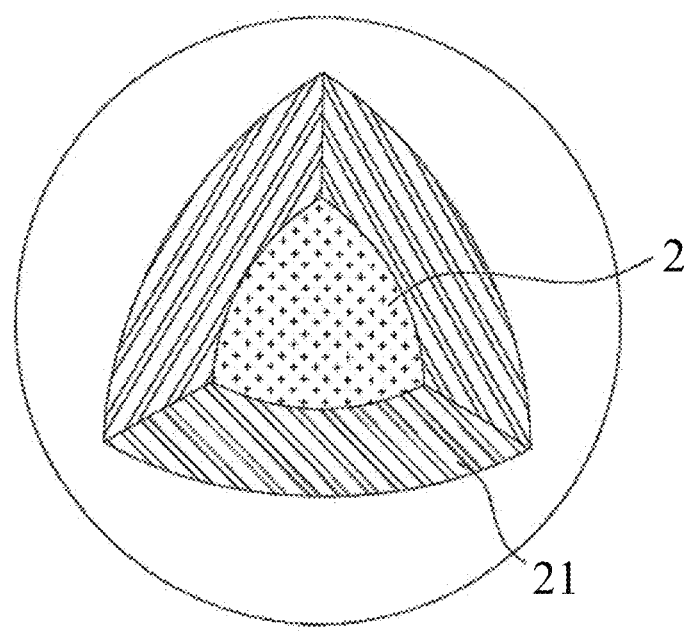
FIG. 3 is another embodiment of the live bacteria-containing particulate of the present invention.

The present invention also relates to a live bacteria-containing particulate, which can be provided by the method of the present invention. As shown in FIGS. 1 and 2, the live bacteria-containing particulate 2 of the present invention comprises a bacterial strain 1, a first covering layer 12 and a second covering layer 14, wherein the first covering layer 12 is in-between the cell membrane 11 and cell wall 13 of the bacterial strain 1 and the bacterial strain 1 is dispersed in the second covering layer 14. In addition, as shown in FIGS. 2 and 3, the live bacteria-containing particulate of the present invention can further comprise a third covering layer 21, wherein the third covering layer 21 is outside the second covering layer 14.

Preferably, the first covering layer comprises at least one of isomalto-oligosaccharide (IMO), lactose, trehalose, galactose, fructose, glucose, maltose, sucrose, fructooligosaccharide (FOS), rhamnose and raffinose. In an embodiment of the present invention, the first covering layer comprises lactose.

Preferably, the second covering layer comprises at least one of maltodextrin, skim milk powder, inulin and starch. In an embodiment of the present invention, the second covering layer comprises maltodextrin.

Preferably, the third covering layer comprises at least one of maltodextrin, arabic gum, chocolate and skim milk powder. More preferably, the third covering layer comprises maltodextrin, skim milk powder or a combination thereof. In an embodiment of the present invention, the third covering layer comprises skim milk powder.

There is no particular limitation to the storage condition of the live bacteria-containing particulate provided in accordance with the present invention, and the storage condition can be adjusted depending on the requirements of transport, storage or use. For example, the live bacteria-containing particulate of the present invention can be placed in a sealed package and stored at room temperature (25° C.), refrigerating temperature (4° C.) or freezing temperature (−20° C.).

The present invention will be further illustrated in detail with specific examples as follows. However, the following examples are provided only for illustrating the present invention and the scope of the present invention is not limited thereby. The scope of the present invention will be indicated in the appended claims.

4. EXAMPLE

4.1 Experimental Methods and Materials 4.1.1 Method of Determining the Viable Bacterial Count The viable bacterial count is determined by the following steps: (i) diluting 50 g solid sample (e.g., live bacteria-containing particulates) or 50 mL liquid sample (e.g., bacterial solution) with 450 mL diluting solution to provide a 10× diluted sample (optionally, the sample can be further diluted by a 10× serial dilution to decrease the concentration of diluted sample); (ii) spreading 1 mL diluted sample onto an agar medium and culturing the agar medium under an anaerobic condition at 37° C. for 72 hours; (iii) observing the agar medium and accounting the number of colonies formed thereon; and (iv) using the agar medium which has 25~250 colonies formed thereon to reverse calculate the viable bacterial count in the sample (unit: CFU/g or CFU/mL).

4.1.2 Culture Conditions for Fermentation
1. Air flow: 3 L/min.
2. Rotor speed: 100 rpm.
3. Dissolved oxygen (DO): no less than 40%.

4.1.3 Fermentation Medium

Pure water was used as a base for preparing a fermentation medium, wherein each liter of pure water was evenly mixed with 30 g of yeast extract, 20 g of yeast peptone, 2 g of dipotassium phosphate, 1 g of magnesium sulfate, 1 g of polysorbate 80, 20 g of glucose and 20 g of 10N sodium hydroxide. The mixture thus obtained was sterilized to provide a fermentation medium (pH 5.5±0.1).

4.1.4 Cryoprotective Agent

Lactose, maltodextrin and skim milk powder were evenly mixed at a weight ratio of 6:1:33 (lactose: maltodextrin: skim milk powder) to provide a cryoprotective agent.

4.2 Preparation Example 4.2.1 Preparation of Bacterial Strain

The collection tube containing *Lactobacillus plantarum* was thawed, and then the strain was inoculated into 150 mL of a MRS broth (purchased from Thermo Fischer Scientific, product name: BD Difco Lactobacilli MRS broth) at an inoculum concentration of 1% (V/V) and cultured under an anaerobic condition at 37° C. for 16 hours, in order to provide a bacterial solution with a viable bacterial count of $1\times10^9$ to $1\times10^{10}$ CFU/mL.

4.2.2 Drawing the Bacterial Growth Curve

The bacterial strain (*Lactobacillus plantarum*) provided by 4.2.1 was inoculated into an MRS broth and cultured at 37° C. During the culture period, the viable bacterial count of the broth was determined every hour through the method of 4.1.1, in order to draw a growth curve of *Lactobacillus plantarum*. The results are shown in FIG. 4.

Figure 4:
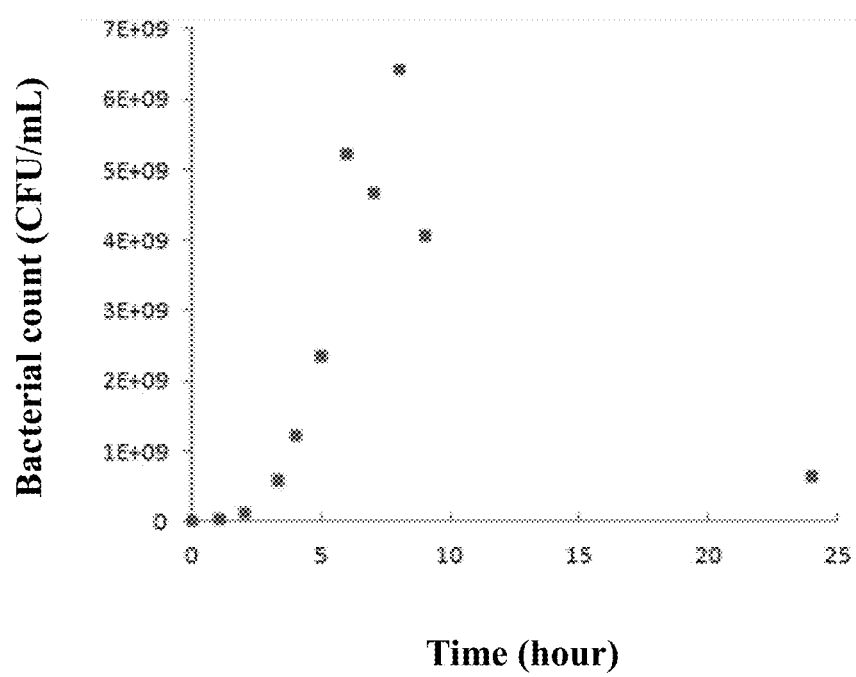
FIG. 4 shows a growth curve of *Lactobacillus plantarum*.

To evaluate the initial time point each of growth logarithmic phase (i.e., $T_1$) and growth stationary phase (i.e., $T_2$) of *Lactobacillus plantarum*, the tangent line slope of each time point shown in FIG. 4 (i.e., a growth curve of *Lactobacillus plantarum*) was calculated by using the "SLOPE" formula of Microsoft Excel. As shown in Table 1 below, the tangent line slope of the growth curve of *Lactobacillus plantarum* at the $2^{nd}$ hour was more than three times that at the $1^{st}$ hour. Therefore, $T_1$ of *Lactobacillus plantarum* was 2. Furthermore, as shown in FIG. 4, the tangent line slope at the $8^{th}$ hour of culture was zero. Therefore, regarding *Lactobacillus plantarum*, $T_2$ was 8.

TABLE 1

| Time (hour) | Bacterial count (CFU/mL) | Tangent line slope |
| --- | --- | --- |
| 0 | $2.5 \times 10^7$ | — |
| 1 | $5 \times 10^7$ | $2.6 \times 10^7$ |
| 2 | $1 \times 10^8$ | $8.7 \times 10^7$ |
| 3.3 | $6 \times 10^8$ | $3.7 \times 10^8$ |
| 4 | $1 \times 10^9$ | $9.1 \times 10^8$ |

4.3 Example 1

4.3.1 Preparation of Bacterial Solution with a High Concentration of Live Bacteria 1. The bacterial strain provided by 4.2.1 was inoculated into a fresh culture broth provided by 4.1.3 at an inoculum concentration of 5% (V/V) (total volume: up to 3 L) and cultured for 2.5 hours to provide a first-stage fermentation broth with a viable bacterial count of $5\times10^8$ to $5\times10^9$ CFU/mL.
2. The first-stage fermentation broth was inoculated into a fresh culture broth provided by 4.1.3 at an inoculum concentration of 6% (V/V) (total volume: up to 50 L) and cultured for 3 hours to provide a second-stage fermentation broth with a viable bacterial count of $5\times10^8$ to $5\times10^9$ CFU/mL.
3. The second-stage fermentation broth was inoculated into a fresh culture broth provided by 4.1.3 at an inoculum concentration of 10% (V/V) (total volume: up to 500 L) and cultured for 7 hours to provide a bacterial solution with a high concentration of live bacteria (viable bacterial count: $5\times10^9$ to $5\times10^{10}$ CFU/mL).

4.3.2 Preparation of Live Bacteria-Containing Particulate

Figure 5:
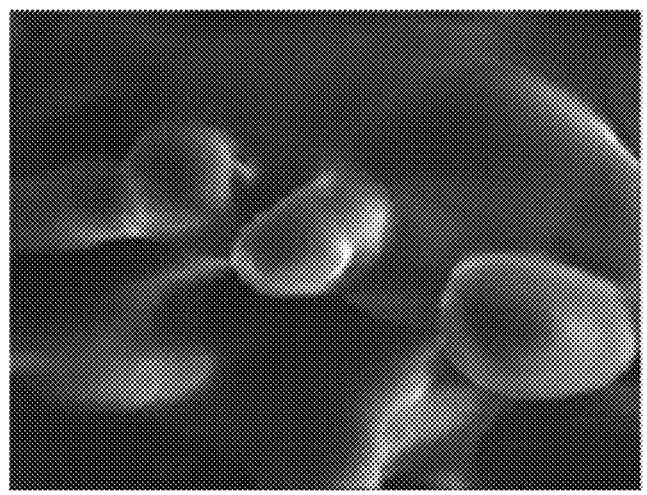
FIG. 5 is a scanning electron microscope image of a mixture of the concentrated bacterial solution provided by the method of the present invention and cryoprotective agents (magnification: 3000×).

The bacterial solution with a high concentration of live bacteria provided by 4.3.1 (total volume: 500 L) was concentrated by using a continuous solid-liquid separator to obtain a concentrated bacterial solution (total volume: 40 L). Thereafter, the concentrated bacterial solution was evenly mixed with pure water and the cryoprotective agent of 4.1.4 at a weight ratio of 2:1:1 (concentrated bacterial solution: pure water:cryoprotective agent) to provide a mixture. An image of the mixture was taken by using a scanning electron microscope (magnification: 3000×) and the result is shown in FIG. 5. As shown in FIG. 5, the aforementioned mixture has a particulate structure.

On the other hand, the aforementioned mixture (including concentrated bacterial solution, pure water and cryoprotective agent) was subjected to a two-stage freeze-drying under vacuum, wherein the first stage is conducted at 10 to 30° C. for about 15 hours, and the second stage is conducted at 30 to 40° C. for about 3 hours, to obtain a live bacteria-containing particulate. Structure of the particulate is shown in FIGS. 1 to 3.

4.4 Example 2

4.4.1 Determination of Viable Bacterial Count in the Live Bacteria-Containing Particulate The live bacteria-containing particulates provided by 4.3.2 were sieved with a 40-mesh sieve (the pore size of 40 mesh sieve is 0.000022597880859375 cm³, and the density of live bacteria-containing particulate is 0.492 g/cm³), to obtain the particulates whose weight is about 0.0000111181573828125 g of each particulate. That is, the viable bacterial count is about $1.11\times10^8$ CFU of each particulate.

The viable bacterial count of the live bacteria-containing particulate provided by 4.3.2 was also determined through the method of 4.1.1. The results show that the viable bacterial count of the live bacteria-containing particulate provided by 4.3.2 is up to $1.3\times10^{12}$ CFU/g. The results indicate that the live bacteria-containing particulate provided in accordance with the present invention has a very high viable bacterial count.

4.4.2 Detection of Residual Moisture in the Live Bacteria-Containing Particulate The residual moisture of the live bacteria-containing particulate provided by 4.3.2 was detected by using a water activity meter (purchased from ROTRONIC company, product no.: HP23-AW-A-SET-40). The result shows that based on the total weight of the live bacteria-containing particulate, the residual moisture was less than 1 wt %. The results indicate that the live bacteria-containing particulate provided in accordance with the present invention has low residual moisture.

The above experimental results show that the method of the present invention can provide a bacterial solution with a high concentration of live bacteria in a short time period, and can further provide a live bacteria-containing particulate with a high viable bacterial count and low residual moisture by using the bacterial solution.

What is claimed is:

1. A method of providing a bacterial solution with a high concentration of live bacteria, comprising
    (a) subjecting a bacterial strain to a three-stage fermentation to obtain a fermentation broth, wherein the three-stage fermentation comprises:
        subjecting a broth of the bacterial strain with a volume of V1 to a first fermentation stage for t1 hour to provide a first-stage fermentation broth, $T_1-2 \leq t1 \leq T_1+2$, and t1 is no less than 0.5,
        diluting and subjecting the first-stage fermentation broth to a second fermentation stage for t2 hour to provide a second-stage fermentation broth, wherein the first-stage fermentation broth is diluted to a volume of V2, V2/V1=10~35, $T_1-2 \leq t2 \leq T_1+2$, and t2 is no less than 0.5, and
        diluting and subjecting the second-stage fermentation broth to a third fermentation stage for t3 hour to provide a third-stage fermentation broth, wherein the second-stage fermentation broth is diluted to a volume of V3, V3/V2=10~35, $T_2-2 \leq t3 \leq T_2+2$, and t3 is no less than 0.5,
    and wherein,
    $T_1$ is an initial time point of growth logarithmic phase of the strain, and
    $T_2$ is an initial time point of growth stationary phase of the strain; and
    (b) concentrating the third-stage fermentation broth to provide a concentrated bacterial solution.

2. The method as claimed in claim 1, wherein $T_1-1 \leq t1 \leq T_1+1$.

3. The method as claimed in claim 1, wherein $T_1-1 \leq t2 \leq T_1+1$.

4. The method as claimed in claim 1, wherein $T_2-2 \leq t3 \leq T_2$.

5. A method of preparing live bacteria-containing particulates, comprising
    (a) subjecting a bacterial strain to a three-stage fermentation to obtain a fermentation broth, wherein the three-stage fermentation comprises:
        subjecting a broth of the bacterial strain with a volume of V1 to a first fermentation stage for t1 hour to provide a first-stage fermentation broth, $T_1-2 \leq t1 \leq T_1+2$, and t1 is no less than 0.5,
        diluting and subjecting the first-stage fermentation broth to a second fermentation stage for t2 hour to provide a second-stage fermentation broth, wherein the first-stage fermentation broth is diluted to a volume of V2, V2/V1=10~35, $T_1-2 \leq t2 \leq T_1+2$, and t2 is no less than 0.5, and
        diluting and subjecting the second-stage fermentation broth to a third fermentation stage for t3 hour to provide a third-stage fermentation broth, wherein the second-stage fermentation broth is diluted to a volume of V3, V3/V2=10~35, $T_2-2 \leq t3 \leq T_2+2$, and t3 is no less than 0.5, and wherein, $T_1$ is an initial time point of growth logarithmic phase of the strain, and $T_2$ is an initial time point of growth stationary phase of the strain, (b) concentrating the third-stage fermentation broth to provide a concentrated bacterial solution;

(c) mixing the concentrated bacterial solution with a protective agent to provide a mixture; and (d) drying the mixture to obtain live bacteria-containing particulates.

6. The method as claimed in claim 5, wherein $T_1-1 \leq t1 \leq T_1+1$.

7. The method as claimed in claim 5, wherein $T_1-1 \leq t2 \leq T_1+1$.

8. The method as claimed in claim 5, wherein $T_2-2 \leq t3 \leq T_2$.

* * * * *